United States Patent [19]

Uphues et al.

[11] Patent Number: 5,108,628
[45] Date of Patent: Apr. 28, 1992

[54] TEXTILE SOFTENERS

[75] Inventors: Guenter Uphues, Monheim; Uwe Ploog, Haan; Klaudia Bischof, Werne; Kaspar Schlueter, Solingen, all of Fed. Rep. of Germany

[73] Assignee: Henkel Kommanditgesellschaft auf Aktien, Duesseldorf-Holthausen, Fed. Rep. of Germany

[21] Appl. No.: 690,885
[22] PCT Filed: Dec. 5, 1989
[86] PCT No.: PCT/EP89/01486
 § 371 Date: Jun. 12, 1991
 § 102(e) Date: Jun. 12, 1991
[87] PCT Pub. No.: WO90/06984
 PCT Pub. Date: Jun. 28, 1990

[30] Foreign Application Priority Data

Dec. 14, 1988 [DE] Fed. Rep. of Germany ....... 3842057

[51] Int. Cl.⁵ .......................................... D06M 10/08
[52] U.S. Cl. ..................... 252/8.6; 252/8.7; 252/8.75; 252/8.8; 252/8.9
[58] Field of Search .............. 252/8.6, 8.7, 8.75, 252/8.8 R, 8.9

[56] References Cited

U.S. PATENT DOCUMENTS 4,661,269  4/1987  Trinh et al. .......................... 252/8.8

FOREIGN PATENT DOCUMENTS 0038862  11/1981  European Pat. Off.
0199382  10/1986  European Pat. Off.
0230910  8/1987  European Pat. Off.

*Primary Examiner*—A. Lionel Clingman
*Assistant Examiner*—William S. Parks
*Attorney, Agent, or Firm*—Ernest G. Szoke; Wayne C. Jaeschke; Real J. Grandmaison

[57] ABSTRACT

Aliphatic carboxylic acid amidoamines obtained by condensation of polyamines and mixtures of carboxylic acids containing aliphatic ether carboxylic acids are useful as textile softeners in baths having a high electrolyte and/or anionic optical brightener content.

11 Claims, No Drawings

TEXTILE SOFTENERS

This invention relates to textile softeners for treatment liquors having high contents of electrolytes and/or anionic optical brighteners.

In the treatment of fabrics, particularly in the crease-resistant finishing of fabrics containing cotton and/or rayon staple, it is standard practice to use softeners in addition to the principal agents (aminoplastic precondensates), cf. Chwala/Anger: "Handbuch der Textilhilfsmittel", pages 464 to 467, Verlag Chemie Weinheim, 1977. The metal salts showing an acidic reaction which are required as catalysts, for example magnesium chloride, aluminum chloride or zinc chloride, impose stringent demands on the electrolyte stability of the softener formulations.

In the case of undyed fabrics, it is standard practice to add anionic optical brighteners to the treatment solutions. However, this means that known cationic softeners, for example fatty amidoamine salts or quaternary ammonium compounds (Chwala/Anger: "Handbuch der Textilhilfsmittel", pages 686 to 687, Verlag Chemie Weinheim, 1977 or U.S. Pat. No. 2,243,980), cannot simultaneously be used because the cationic softeners react chemically with the anionic brighteners and lead to precipitations. To prevent the formation of precipitable electroneutral compounds, therefore, cationic softeners modified by incorporation of polyethylene glycol chains, for example fatty acid amidoamines reacted with ethylene oxide or reactive polyglycol derivatives, for example chlorohydrin or glycidyl ethers, are used in many cases (Lindner: "Tenside - Textilhilfsmittel Waschrohstoffe", Vol. 1, page 975 (1974)). However, the use of modified softeners such as these is attended by a number of disadvantages. For example, the feel properties of the textile material are adversely affected. The ethoxylation of fatty acid amidoamines often results in visible discoloration of the treated textile material. The modification of fatty acid amidoamines with chlorohydrin ethers must be carried out in the presence of alkali hydroxides. The sodium chloride formed as secondary products during this reaction leads to difficulties in the production of aqueous dispersions. In many cases, the aqueous dispersions are obtained are only stable for short periods, for example for 2 hours, and/or have high viscosities.

Now, the problem addressed by the present invention was to develop textile softeners which would be stable in the presence of electrolytes and/or anionic optical brighteners. In addition, the softeners to be developed would provide the textile material with the favorable feel properties obtainable with cationic softeners known from the prior art and would not have any of the disadvantages involved in using fatty acid amidoamines modified with ethylene oxide or with reactive polyglycol derivatives.

It has surprisingly been found that the stringent demands made of textile softeners are satisified by aliphatic carboxylic acid amidoamines which are obtained by reaction of polyamines with carboxylic acid mixtures containing ether carboxylic acids.

Accordingly, the present invention relates to textile softeners for treatment liquors having high contents of electrolytes and/or anionic optical brighteners, characterized in that the treatment liquors contain as textile softeners aliphatic carboxylic acid amidoamines obtainable by condensation of polyamines and carboxylic acid mixtures containing aliphatic ether carboxylic acids corresponding to general formula I

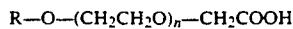

in which R represents $C_{8-18}$ alkyl or $C_{8-18}$ alkenyl or $CH_2$—COOH and n is a number of 2 to 20, in combination with aliphatic $C_{8-22}$ monocarboxylic acids and/or amide-forming aliphatic $C_{8-22}$ monocarboxylic acid derivatives.

In the context of the invention, "textile softeners" are understood to be auxiliaries which impart good feel properties, for example, to yarns, nonwovens, flat textile materials and/or knitted fabrics containing natural and/or synthetic fibers.

Suitable polyamine components for the preparation of the aliphatic carboxylic acid amidoamines to be used in accordance with the invention are, preferably, those corresponding to general formula II

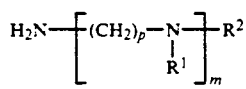

in which $R^1$ is hydrogen, methyl, ethyl or hydroxyethyl and $R^2$ is hydrogen, methyl, ethyl, hydroxyethyl or —$(CH_2)_p$—$NHR^1$, m is an integer of 1 to 4 and p is an integer of 2 to 4. Diethylenetriamine, triethylenetetramine, tetraethylenepentamine, dimethylaminopropyl amine, propylenediamine, di(trimethylene)triamine and/or aminoethyl ethanolamine are examples of suitable polyamines. Diethylenetriamine and/or aminoethyl ethanolamine are particularly preferred.

The aliphatic $C_{8-22}$ monocarboxylic acids, which may be present in the carboxylic acid mixtures, are saturated and/or unsaturated, natural and/or synthetic fatty acids or fatty acid mixtures, for example caprylic acid, capric acid, lauric acid, myristic acid, palmitic acid, stearic acid, oleic acid, coconut oil fatty acid, tallow fatty acid and/or rapeseed oil fatty acid. Amide-forming derivatives of aliphatic $C_{8-22}$ monocarboxylic acids are understood to be the esters derived from the above-mentioned saturated and/or unsaturated, natural and/or synthetic fatty acids or fatty acid mixtures with lower alkyl alcohols, for example methanol or ethanol, fatty acid glycerides and/or fatty acid halides. The ether carboxylic acids corresponding to general formula I present in the carboxylic acid mixtures are commercial products and may be obtained, for example, by reaction of ethoxylated $C_{8-18}$ alkyl and/or $C_{8-18}$ alkenyl alcohols and/or polyglycols with sodium chloroacetate. The ethoxylated alkyl and/or alkenyl alcohols required for these reactions may be obtained by ethoxylation of alkyl and/or alkenyl alcohols of natural and/or synthetic origin with ethylene oxide by known industrial methods ("Chemische Technologie", Vol. 7, pages 131 to 132, Carl Hanser-Verlag, München, 1986). Alkyl and/or alkenyl alcohol mixtures of natural origin, for example $C_{12-18}$ fatty alcohol mixtures or tallow alcohol, are preferably used.

The carboxylic acid mixtures containing aliphatic ether carboxylic acids in combination with aliphatic $C_{8-22}$ monocarboxylic acids and/or amide-forming aliphatic $C_{8-22}$ monocarboxylic acid derivatives are reacted with polyamines at temperatures of 80° to 200° C. to an acid value of 0 to 10. To obtain a further improvement in stability, it can be of advantage partly to acylate the carboxylic acid amidoamines obtained with $C_{1-4}$ carboxylic acid derivatives, for example acetic anhydride, at temperatures of 40° to 140° C. The ether carboxylic acid content of the carboxylic acid mixtures is selected so that the carboxylic acid amidoamines used in accordance with the invention as textile softeners have an ethylene oxide content of 3 to 15% by weight. The optionally acylated carboxylic acid amidoamines are then optionally, nonionic surfactants, for example alkoxylated alkyl and/or alkenyl alcohols, alkoxylated alkylaryl phenols and/or alkoxylated $C_{8-22}$ alkyl and/or $C_{8-22}$ alkenyl amines are added to the resulting melt at temperatures of 60° to 95° C. Suitable lower organic acids are optionally hydroxyl-substituted mono- and/or polycarboxylic acids, for example acetic acid, glycolic acid, lactic acid and/or citric acid; suitable lower inorganic acids are, for example, hydrochloric acid and/or phosphoric acid. The solids content, i.e. the content of carboxylic acid amidoamines and, optionally, nonionic surfactants, of the aqueous dispersions obtained is between 5 and 30% by weight and preferably between 15 and 25% by weight. The content of nonionic surfactants in the aqueous dispersions is between 0 and 25% by weight, based on the content of carboxylic acid amidoamines.

The softeners according to the invention may readily be used in the form of aqueous dispersions in treatment liquors having a high content of electrolytes and/or anionic optical brighteners, such as finishing and/or dye liquors. For the finishing of, for example, yarns, flat textile materials or knitted fabrics containing natural and/or synthetic fibers, the textile material is impregnated in known manner with an aqueous finishing liquor containing per liter of liquor from 3 to 20 g active substance carboxylic acid amidoamines, 30 to 100 g active substance fixing agents, for example dimethylol dihydroxyethylene urea, 5 to 15 g catalysts, for example magnesium chloride, 0 to 5 g anionic optical brighteners and 0 to 10 g nonionic surfactants, passed over squeezing rolls subsequently dried at temperatures of 100° to 130° C. and then condensed at temperatures of 150° to 190° C., for example over a period of 3 minutes. Aqueous dye liquors containing 1 to 5% by weight dyes, 0.1 to 1% by weight active substance carboxylic acid amidoamines, 0 to 0.5% by weight nonionic surfactants, based on the weight of the textile, and 1 to 10 g electrolytes, for example sodium sulfate, per liter of liquor are normally applied to the textile material by the extraction method.

The carboxylic acid amidoamines according to the invention show excellent stability to electrolytes and/or anionic optical brighteners. Irrespective of the type of fiber substrate, good feel properties are imparted to the textile materials where the softeners according to the invention are used in treatment liquors and, in particular, in dye liquors and/or finishing liquors.

EXAMPLES

The amine nitrogen content was determined by titration with perchloric acid in acetic acid medium; the acid values were determined by DGF method C-V2.

EXAMPLE 1

Production of Softener A According to the Invention

In a stirred reactor equipped with a thermometer, an inlet pipe for inert gas and a descending condenser, a mixture of 540 g (2.0 mol) of a hydrogenated fatty acid based on tallow fatty acid and 135 g (0.3 mol) of an ether carboxylic acid, obtained by reaction of a lauryl/myristyl alcohol mixture (70% by weight $C_{12}$, 30% by weight $C_{14}$) with 3.8 mol ethylene oxide per hydroxyl group and subsequent reaction with sodium chloroacetate, was reacted with 118.5 g (1.15 mol) diethylenetriamine at 80° C. The temperature increased to 123° C. by the exothermic nature of the reaction was further increased until the distillation of water of reaction began at 145° C. After another increase in temperature, the reaction mixture was finally stirred for 1 hour at 200° C. A total of 45 g distillate was obtained. The reaction product contained 2.14% by weight amine nitrogen and had an acid value of 5.8.

57.2 g acetic anhydride were added to the reaction product at 120° C., followed by stirring for 30 minutes at 120 to 125° C. 808 g of a yellow solid were obtained, of which the analysis showed 1.06% by weight amine nitrogen and an acid value of 44.7.

To prepare an aqueous dispersion containing 20% by weight solids, 92 g of the acylated reaction product were melted and 23 g tallow alkyl polyglycol ether containing 14 ethylene oxide units, 1.0 g 100% by weight acetic acid, 4.5 g urea and 479.5 g water were successively added to the resulting melt at 85 to 90° C. After complete homogenization and cooling to 20° C., 600 g of a fine-particle, free-flowing dispersion were obtained; the dispersion could be readily further diluted with cold water. The pH value of the aqueous dispersion after dilution with 10 times the quantity of water was 5.3.

EXAMPLE 2

Production of Softener B According to the Invention

A mixture of 277.3 g (1.03 mol) of a hydrogenated fatty acid based on tallow and 30.1 g (0.12 mol) of a technical trioxaundecanedioic acid was reacted as in Example 1 with 65.5 g (0.64 mol) diethylenetriamine. After removal of 23 g distillate, the product contained 2.58% by weight amine nitrogen. The acid value determined by DGF method C-V2 was 5.8.

150 g of the reaction product were acylated as in Example 1 with 14.2 g (0.14 mol) acetic anhydride. 163 g of a light yellow solid having an amine nitrogen content of 1.23% by weight and an acid value of 53.8 were obtained.

An aqueous dispersion containing 20% by weight solids was prepared as in Example 1 from 60 g of the acylated reaction product, 0.5 g 100% by weight acetic acid and 241.5 g water. 302 g of the free-flowing dispersion readily miscible with cold water were obtained; after dilution with 10 times the quantity of water, the dispersion had a pH value of 4.5.

EXAMPLE 3:

Production of Softener C According to the Invention

A mixture of 328.4 g (1.22 mol) of a hydrogenated fatty acid based on tallow and 29.9 g (0.04 mol) of an ether carboxylic acid obtained by reaction of a technical fatty alcohol (53% by weight $C_{12}$, 22% by weight $C_{14}$, 10% by weight $C_{16}$, 15% by weight $C_{18}$) with 10 mol ethylene oxide/hydroxyl group and subsequent reaction with sodium chloroacetate, was reacted as in Example 1 with 64 g (0.62 mol) diethylenetriamine. After the removal of 26 g distillate, the reaction product contained 2.1% by weight amine nitrogen and had an acid value of 6.3.

150 g of the reaction product were acylated as in Example 1 with 11.5 g (0.113 mol) acetic anhydride. 161 g acylated reaction product having an amine nitrogen content of 1.09% by weight and an acid value of 35.5 were obtained.

An aqueous dispersion containing 20% by weight solids was prepared as in Example 1 from 60 g of the acylated reaction product, 1.3 g 60% by weight acetic acid and 243.7 g water. 305 g of a medium-viscosity dispersion readily miscible with cold water were obtained. After dilution with 10 times the quantity of water, the dispersion had a pH value of 4.3.

EXAMPLE 4

Production of Softener D According to the Invention

A mixture of 1,072 g (3.97 mol) of a hydrogenated fatty acid based on tallow and 186.6 g (0.41 mol) of the ether carboxylic acid of Example 1 was reacted as in Example 1 with 304 g (2.92 mol) aminoethyl ethanolamine. The reaction product, which contained 1.82% by weight amine nitrogen after the removal of 80 g distillate, was then acylated with 48.1 g (0.42 mol) acetic anhydride at 100° C. 1,523 g of an end product solid at room temperature containing 1.26% by weight amine nitrogen and having an acid value of 29.8 were obtained after stirring for 30 minutes at 100° C.

An aqueous dispersion containing 25% by weight solids was prepared as in Example 1 from 200 g of the acylated reaction product, 7.1 g 100% by weight acetic acid, 50 g tallow alkyl polyglycol ether containing 15 ethylene oxide units and 742.9 g water. 1,000 g of a medium-viscosity dispersion readily miscible with cold water were obtained.

EXAMPLE 5

Softener E) (Comparison)

A mixture of 137.5 g (0.16 mol) hydrogenated beef tallow and 16.8 g (0.16 mol) aminoethyl ethanolamine was stirred at 95 to 100° C. to an amine nitrogen content of 1% by weight. After addition of 15 g (0.14 mol) 70% glycolic acid, 96 g tallow alkyl polyglycol ether containing 14 ethylene oxide units were added to the reaction mixture and, finally, the mixture was diluted with 1,020 g water to a solids content of 20% by weight. A medium-viscosity dispersion readily miscible with water was obtained.

EXAMPLE 6

Softener F (Comparison)

768.4 g (0.9 mol) hydrogenated beef tallow were mixed at 90° C. with 148.9 g (0.77 mol) technical tetraethylenepentamine and 2.0 g sodium methylate solution (30% by weight). The reaction mixture was then heated to 200° C. and stirred at that temperature for 3.5 hours. 49.0 g of a bis-chlorohydrin ether (reaction product of polyethylene glycol having an average molecular weight of 600 and 2 mol epichlorohydrin) and 31.4 g 20% by weight aqueous sodium hydroxide were then added at 80° C. to the product obtained, which had an amine nitrogen content of 1.95% by weight, followed by stirring for 75 minutes at 80° C. 1,000 g of a mass solid at room temperature were obtained.

To prepare an aqueous dispersion containing 20% by weight solids, 100 g of the reaction product, 26 g 60% by weight acetic acid and 374 g water were stirred at 80° C. to form a homogeneous mixture. 500 g of a medium-viscosity dispersion were obtained.

APPLICATION EXAMPLES

Stability to Anionic Optical Brighteners

Cotton fabric was treated by padding with a crease-resistant finish liquor containing per liter of liquor 100 g Stabitex FRD, a product of Henkel KGaA (dimethylol dihydroxyethylene urea, active substance content: 50% by weight), 10 g magnesium chloride, 5 g Blankophor BBU flüssig, a product of Bayer AG (anionic optical brightener) and 30 g of an aqueous dispersion prepared in accordance with any of Examples 1 to 6 containing any of the softeners A to F (liquor uptake 60%). After drying at 100° C., condensation was carried out for 3 minutes at 150° C.

Table 1 below shows the liquor stabilities after 24 hours and the brightening effects on the fabric.

TABLE 1

| Softener | | Liquor stability after 24 hours | Brightening effect on the fabric |
|---|---|---|---|
| A | Invention | + | +* |
| B | | + | +* |
| C | | + | +* |
| D | | + | +* |
| E | Prior art | + | +* |
| F | | − | −* |

+ stable, − precipitates, +* no deterioration in the brightening effects, −* no brightening effects

FEEL

A woven cotton poplin fabric and a knitted cotton/polyester fabric were treated by padding with crease-resistant finish liquors containing per liter of liquor 100 g Stabitex FRD, a product of Henkel KGaA, 10 g magnesium chloride and 30 g of an aqueous dispersion prepared in accordance with any of Examples 1 to 6 containing any of softeners A to F (liquor uptake 60%). After drying at 100° C., condensation was carried out for 3 minutes at 160° C.

Feel was evaluated by six people by comparison with a woven fabric obtained without any addition of softener. The results are shown in Table 2 below.

TABLE 2

| Softener | | Feel Woven cotton poplin fabric | Knitted cotton/polyester fabric |
|---|---|---|---|
| — | | — — | — — |
| A | Invention | + | + |
| B | | + | + |
| C | | + | + |
| D | | +− | + |
| E | Prior art | − | − |
| F | | +− | + |

+ good, +− average, − poor, − − very poor

We claim:

1. A textile softener for a treatment liquor having a high content of electrolytes or anionic optical brighteners, said textile softener comprising an aliphatic carboxylic acid amidoamine obtained by condensing a polyamine and carboxylic acid mixtures containing aliphatic ether carboxylic acids corresponding to formula I $$R-O-(CH_2CH_2O)_n-CH_2COOH \quad (I)$$

in which R represents $C_{8-18}$ alkyl or $C_{8-18}$ alkenyl radical or $CH_2$—COOH and n is a number of 2 to 20, in combination with an aliphatic $C_{8-22}$ monocarboxylic acid or amide-forming aliphatic $C_{8-22}$ monocarboxylic acid derivative.

2. A textile softener as in claim 1 wherein said polyamine corresponds to formula II

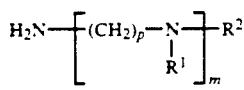
(II)

in which $R^1$ is hydrogen, methyl, ethyl or hydroxyethyl, $R^2$ is hydrogen, methyl, ethyl, hydroxyethyl or $(CH_2)_p$—$NHR^1$, m is an integer of 1 to 4, and p is an integer of 2 to 4.

3. A textile softener as in claim 1 wherein said aliphatic carboxylic acid amidoamine is partly acylated with a $C_{1-4}$ carboxylic acid derivative.

4. A textile softener as in claim 1 wherein the ethylene oxide content of said aliphatic carboxylic amidoamine is between 3 to 15% by weight.

5. A textile softener as in claim 1 wherein said polyamine is selected from the group consisting of diethylenetriamine, triethylenetetramine, tetraethylenepentamine, dimethylaminopropyl amine, propylene diamine, di(trimethylene) triamine, and aminoethyl ethanolamine.

6. The process of softening a textile in a treatment liquor having a high content of electrolytes or anionic optical brighteners, comprising contacting said textile with a textile softener comprising an aliphatic carboxylic acid amidoamine obtained by condensing a polyamine and carboxylic acid mixtures containing aliphatic ether carboxylic acids corresponding to formula I $$R—O—(CH_2CH_2O)_n—CH_2COOH \qquad (I)$$

in which R represents $C_{8-18}$ alkyl or $C_{8-18}$ alkenyl radical or $CH_2$—COOH and n is a number of 2 to 20, in combination with an aliphatic $C_{8-22}$ monocarboxylic acid or amide-forming aliphatic $C_{8-22}$ monocarboxylic acid derivative.

7. The process as in claim 6 wherein said polyamine corresponds to formula II

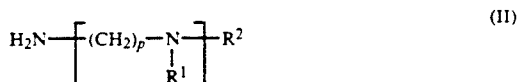
(II)

in which $R^1$ is hydrogen, methyl, ethyl or hydroxyethyl, $R^2$ is hydrogen, methyl, ethyl, hydroxyethyl or $(CH_2)_p$—$NHR^1$, m is an integer of 1 to 4, and p is an integer of 2 to 4.

8. The process as in claim 6 wherein said aliphatic carboxylic acid amidoamine is partly acylated with a $C_{1-4}$ carboxylic acid derivative.

9. The process as in claim 6 wherein the ethylene oxide content of said aliphatic carboxylic amidoamine is between 3 to 15% by weight.

10. The process as in claim 6 wherein said softener is in the form of an aqueous dispersion.

11. The process as in claim 6 wherein said polyamine is selected from the group consisting of diethylenetriamine, triethylenetetramine, tetraethylenepentamine, di(trimethylene) triamine, and aminoethyl ethanolamine.

* * * * *